United States Patent [19]

Drent et al.

[11] Patent Number: 5,719,313

[45] Date of Patent: Feb. 17, 1998

[54] CARBONYLATION CATALYST SYSTEM AND A PROCESS FOR THE CARBONYLATION OF ACETYLENICALLY UNSATURATED COMPOUNDS

[75] Inventors: Eit Drent; Willem Wabe Jager, both of Amsterdam, Netherlands

[73] Assignee: Shell Oil Company, Houston, Tex.

[21] Appl. No.: 614,563

[22] Filed: Mar. 13, 1996

[30] Foreign Application Priority Data

Mar. 16, 1995 [EP] European Pat. Off. .............. 95200643

[51] Int. Cl.$^6$ .................. C07C 67/36; C07C 51/14; C07C 67/38; C07C 69/54; B01J 31/02; B01J 31/24

[52] U.S. Cl. .................. 560/207; 560/97; 560/104; 554/129

[58] Field of Search ............... 560/207; 502/167

[56] References Cited

U.S. PATENT DOCUMENTS

| 4,739,109 | 4/1988 | Drent .................. | 560/207 |
|---|---|---|---|
| 4,739,110 | 4/1988 | Drent .................. | 560/207 |
| 4,831,187 | 5/1989 | Drent .................. | 560/107 |
| 4,940,787 | 7/1990 | Drent .................. | 536/124 |
| 5,028,576 | 7/1991 | Drent et al. .................. | 502/167 |
| 5,099,062 | 3/1992 | Drent et al. .................. | 560/207 |
| 5,103,043 | 4/1992 | Drent et al. .................. | 560/207 |
| 5,149,868 | 9/1992 | Drent .................. | 562/497 |
| 5,158,921 | 10/1992 | Drent et al. .................. | 502/167 |
| 5,166,411 | 11/1992 | Drent .................. | 560/207 |
| 5,177,253 | 1/1993 | Drent et al. .................. | 560/207 |
| 5,179,225 | 1/1993 | Drent et al. .................. | 560/207 |
| 5,189,003 | 2/1993 | Klusener et al. .................. | 502/167 |
| 5,258,546 | 11/1993 | Klusener et al. .................. | 560/207 |
| 5,350,876 | 9/1994 | Drent et al. .................. | 560/207 |
| 5,414,109 | 5/1995 | Drent et al. .................. | 560/207 |
| 5,436,356 | 7/1995 | Drent et al. .................. | 554/129 |

FOREIGN PATENT DOCUMENTS

| 0233759 | 8/1987 | European Pat. Off. .............. | 560/207 |
|---|---|---|---|
| 0441446 | 8/1991 | European Pat. Off. .............. | 560/307 |
| 0565199 | 10/1993 | European Pat. Off. .............. | 560/207 |
| WO95/05357 | 2/1995 | WIPO .................. | 560/207 |

*Primary Examiner*—Floyd D. Higel
*Attorney, Agent, or Firm*—Del S. Christensen

[57] ABSTRACT

The invention relates to a novel carbonylation catalyst system and a process for the carbonylation of acetylenically unsaturated compounds, whereby a feedstock, comprising an acetylenically unsaturated compound and a relatively minor amount of an 1,2-alkadiene compound, is contacted under carbonylation conditions with carbon monoxide and a hydroxylated co-reactant in the presence of the novel carbonylation catalyst system that is based on:

a) a source of cations of one or more metals of Group VIII of the Periodic Table;

b) a phosphine of the general formulae $PR^1R^2R^3$, $R^1R^2M-R-PR^3R^3$, or $R^2R^3M-R-PR^1R^3$, wherein $R^1$ represents a substituted or non-substituted 6-membered heteroaryl group having at least one imino nitrogen atom next to the carbon atom that is attached to the phosphorus atom; $R^2$ represents a halogenated aryl group; $R^3$ or each of the $R^3$'s represents a substituted or non-substituted (hetero)hydrocarbyl group, M is an element of Group Va, preferably a nitrogen or phosphorus atom, R represents a bridging (substituted) hydrocarbyl group having 1 to 4 carbon atoms in the bridge; and c) a source of protons.

11 Claims, No Drawings

CARBONYLATION CATALYST SYSTEM AND A PROCESS FOR THE CARBONYLATION OF ACETYLENICALLY UNSATURATED COMPOUNDS

FIELD OF THE INVENTION

The invention relates to a novel carbonylation catalyst system and a process for the carbonylation of acetylenically unsaturated compounds, whereby a feedstock, comprising an acetylenically unsaturated compound and a relatively minor amount of an 1,2-alkadiene compound, is contacted under carbonylation conditions with carbon monoxide and a hydroxylated co-reactant in the presence of the novel carbonylation catalyst system.

BACKGROUND TO THE INVENTION

Generally, the feedstocks available for the carbonylation of acetylenically unsaturated compounds additionally contain 1,2-alkadiene compounds (so-called allenes). Typically, the presence of these 1,2 alkadiene compounds, even in relatively small amounts (say up to 0.4%), unfavorably affects the activity of the catalyst system. Therefore, special measures to purify the feedstocks need to be taken, before they can be used for the carbonylation process.

In International application WO 95/05357, a carbonylation catalyst system is disclosed, that comprises a certain (mono or bidentate) (di)phosphine bearing for instance 6-halo-2-pyridyl groups on the phosphorus atom as ligand to the transition metal, that easily outperforms the already fine catalyst system disclosed in EP-A-0,441,446 and even performs satisfactorily in the presence of 7.0% v of 1,2-alkadiene impurities. However, it remains desirable to be able to use alternative catalyst systems of at least similar competence. Moreover, as the carbonylation reaction produces heat, a carbonylation catalyst system is looked for that on the one hand can feed on feedstocks comprising an acetylenically unsaturated compound and a relatively minor amount of an 1,2-alkadienes, and on the other hand is stable at temperatures in the range of 70 to 100° C.

SUMMARY OF THE INVENTION

The invention may be defined as relating to a novel carbonylation catalyst system and to a process for the carbonylation of acetylenically unsaturated compounds, whereby a feedstock comprising an acetylenically unsaturated compound and a relatively minor amount of an 1,2-alkadiene compound is contacted under carbonylation conditions with carbon monoxide and a hydroxylated co-reactant, in the presence of the novel catalyst system. The novel catalyst system is based on:

a) a source of cations of one or more metals of Group VIII of the Periodic Table;

b) a phosphine of the general formulae $PR^1R^2R^3$, $R^1R^2M-R-PR^3R^3$, or $R^2R^3M-R-PR^1R^3$, wherein $R^1$ represents a substituted or non-substituted 6-membered heteroaryl group having at least one imino nitrogen atom next to the carbon atom that is attached to the phosphorus atom; $R^2$ represents a halogenated aryl group; $R^3$ or each of the $R^3$'s represents a substituted or non-substituted (hetero) hydrocarbyl group, M is an element of Group Va, preferably a nitrogen or phosphorus atom, R represents a bridging (substituted) hydrocarbyl group having 1 to 4 carbon atoms in the bridge; and c) a source of protons.

DESCRIPTION OF THE PREFERRED EMBODIMENT

The metals as regards component a) of the catalyst system include iron, cobalt, ruthenium, rhodium, iridium, and osmium, but in particular nickel, palladium and platinum. Preferably, the catalyst system is based on a source of palladium cations.

The source of cations of metals of Group VIII may be the metallic element or a metal compound, such as a metal salt or a complex of the metal with a phosphine, with carbon monoxide or with acetylacetonate. It is advantageously a metal compound, in particular a metal salt. Examples of suitable metal salts are salts of sulfuric acid, nitric acid, sulfonic acids, phosphonic acids, perhalic acids and carboxylic acids, such as alkane carboxylic acids with 1 to 12 carbon atoms, for example acetic acid and propionic acid, or halogenated carboxylic acids, for example trichloroacetic acid and trifluoroacetic acid. Palladium acetate has proved to be a particularly suitable source of metal cations.

As regards component b) of the catalyst system, $R^1$ may for instance be a 2-pyridyl-, or the radical of any of the diazines, triazines or tetrazines. Moreover, the 6-membered ring system may be part of a larger, fused ring system (e.g., (iso)quinolinyl-, a radical of any of the benzodiazines or benzotriazines). Preferably, the phosphine is substituted with a 2-pyridyl group. Suitable substituents on the 6-membered heteroaryl group include alkyl groups, for example methyl and ethyl groups, amino and (di)alkylamino groups and halogen atoms.

$R^2$ is a phenyl group or a larger aryl group having at least one or more halogen atoms substituted thereon. Suitably, the halogen atoms are chlorine or bromine atoms. More suitably, $R^2$ is a phenyl group having one or more chlorine atoms substituted thereon. The location of the or each halogen atom is not very important, i.e., excellent results have been achieved with meta-chlorine substituents.

$R^3$ or each of the $R^3$'s preferably represents a substituted or unsubstituted pyridyl, alkyl or aryl group, and—more preferably—is identical to either $R^1$ or $R^2$. Examples of suitable $R^3$ groups are 2-pyridyl, phenyl, tolyl, xylyl, and cyclohexyl groups and alkyl groups having from 3 to 7 carbon atoms. Phosphines wherein both $R^2$ and $R^3$ represent a halogenated phenyl group are preferred.

Preferably, the phosphine is a monophosphine of the general formula $PR^1R^2R^3$.

As regards component c) of the catalyst system, the source of protons may be provided by a protonic acid or even traces water. Indeed, the protonic acid may be generated in situ, for instance, upon addition of a Lewis acid to the hydroxylated co-reactant, or by carbonylation of the acetylenically unsaturated compound with water into the corresponding acid. Lewis acids that are suitably used include halogenated arylborates, $BF_3$, $AlCl_3$, $SnF_2$, $Sn(CF_3SO_3)_2$, $SnCl_2$, $GeCl_2$ and $PF_5$.

Preferably, the protonic acid has a substantially non-coordinating anion, i.e. an anion which does not, or only to a very minor extent, coordinate with the metal of Group VIII. Preferred acids in this respect include: sulfuric acid; sulfonic acids; halogenated carboxylic acids such as trifluoroacetic acid; perhalic acids such as perchloric acid, and acidic ion exchange resins such as a sulphonated ion exchange resin. Optionally substituted alkylsulfonic acids, such as methanesulfonic acid, trifluoromethanesulfonic acid and tert-butylsulfonic acid are examples of very preferred protonic acids.

The number of moles of phosphine and of moles of protonic acid per mole (of atoms) of the metal of Group VIII may vary considerably. Recommended phosphine amounts are in the range of 10 to 100 moles of phosphine per mole of the metal of Group VIII and in particular in the range of 20 to 80. The amount of protonic acid is preferably selected such that per mole of the metal of Group VIII, 2 to 500 moles of protonic acid are present.

The catalyst system of the invention may be homogeneous or heterogeneous. Preferably, it is homogeneous. The amount in which the catalyst is applied in the process of the invention is suitably selected such that per mole of acetylenically unsaturated compound to be converted, from $10^{-8}$ to $10^{-1}$ mole of the Group VIII metal is present, preferably from $10^{-7}$ to $10^{-2}$ on the same basis.

Suitable acetylenically unsaturated compounds, to be used as starting material in the process of the invention, include optionally substituted alkynes with 2 to 20 carbon atoms per molecule. Examples are acetylene, propyne, 1-butyne, 2-butyne, 1-hexyne, phenyl acetylene and benzylethyne. Preferably, unsubstituted alkynes with 3 to 10 carbon atoms are used.

In view of the industrial outlets for the carbonylated products, propyne is a preferred starting material.

As has been stated above, a major advantage of the catalyst systems of the invention consists in their tolerance towards 1,2-alkadiene compounds in the acetylenic feedstocks. Accordingly, commercially available feedstocks may be used that containing small amounts of 1,2-alkadiene compounds, such as propadiene, in addition to the acetylenically unsaturated compounds. In general, a 1,2-alkadiene content of at most 0.1 mole per mole (e.g., 10%), based on acetylenically unsaturated compound, can be tolerated. It is recommended to use feedstocks in which the amount of 1,2alkadiene compounds is lower, suitably in the range of 0.002 to 0.05 moles per mole of acetylenically unsaturated compound.

The hydroxylated co-reactant may be any hydroxyl-containing compound such as a monohydric, dihydric or polyhydric alkanol, a phenol, or water.

Monohydric alkanols are preferred, in particular those having from 1 to 4 carbon atoms. Among these, methanol is most preferred.

The co-reactant is suitably used in excess, thereby avoiding the need of a separate diluent or solvent. However, a liquid diluent may be applied, if so desired. Preferably, non-alkaline diluents are used, such as ketones, e.g. methylisobutylketone, or ethers, e.g. dipropylether or 2,5,8-trioxanonane.

Owing to the high activity of the catalysts, the process of the invention proceeds readily at moderate reaction conditions. Suitable reaction temperatures are, for instance, in the range of 20 to 150° C., preferably in the range of 30 to 100° C.

The reaction pressure is usually selected in the range of 1 to 100 bar. Preferably, the pressure is in the range of 5 to 70 bar.

The invention is illustrated with the following, non-limiting examples.

EXAMPLES

All experiments were carried out in a 250 ml "Hastelloy C" (trade mark) magnetically stirred autoclave. The autoclave was charged with 0.025 mmoles (5.6 mg) of palladium (II) acetate, the selected phosphine and protonic acid in the amounts indicated hereafter, and 50 ml of methanol.

Air was evacuated from the autoclave, whereupon 30 ml of a feedstock containing propyne and propadiene was added.

Subsequently, carbon monoxide was supplied up to a pressure of 60 bar. The autoclave was sealed and heated to the desired reaction temperature.

As soon as the falling pressure remained constant (marking the completion of the reaction), the contents of the autoclave were cooled and a sample was withdrawn and analyzed by gas liquid chromatography.

Example I a) An experiment was carried out in the manner as outlined above, whereby as phosphine 2 mmol (0.53 g) of bisphenyl(2-pyridyl)phosphine and as protonic acid 2 mmol (130 µl) of methanesulfonic acid was used. The feed was propyne, containing 1.9% of propadiene. The reaction temperature was 90 C.

The reaction time (completion) was 1 hour. Analysis showed that methyl methacrylate (MMA) had been formed with a selectivity of 98.7% at a propyne conversion of about 100%. The average reaction rate was calculated to be 25,800 moles of product per mole of palladium and per hour (mol/mol.hr).

b) The experiment described under a) was repeated at 80° C. with the difference that as phosphine 2 mmol (0.66 g) of bis(3-chlorophenyl)(2-pyridyl)phosphine was used.

The reaction time was 1 hour. Analysis showed that MMA had been formed with a selectivity of about 98.5% at a propyne conversion of about 100%. The average reaction rate was calculated to be 50,000 mol/mol.hr.

Example II a) An experiment was carried out in the manner as outlined above, whereby as phosphine 1 mmol (0.26 g) of bisphenyl(2-pyridyl)phosphine and as protonic acid 2 mmol (130 µl) of methanesulfonic acid were used. The feed was propyne, containing 2.3% of propadiene. The reaction temperature was 90° C.

The reaction time (completion) was 5 hours. Analysis showed that MMA had been formed with a selectivity of 98.6% at a propyne conversion of about 84%. The average reaction rate was calculated to be 5,000 mol/mol.hr.

b) The experiment described under a) was repeated at 80° C. with the difference that as phosphine 1 mmol (0.33 g) of bis(3-chlorophenyl)(2-pyridyl)phosphine was used.

The reaction time was 10 hours. Analysis showed that MMA had been formed with a selectivity of 98.5% at a propyne conversion of about 86%. The average reaction rate was calculated to be 7,200 mol/mol.hr.

c) The experiment described under b) was repeated with the difference that as phosphine 2 mmol (0.66 g) of bis(3-chlorophenyl)(2-pyridyl)phosphine was used.

The reaction time was 2 hours. Analysis showed that MMA had been formed with a selectivity of 98.5% at a propyne conversion of about 100%. The average reaction rate was calculated to be 48,800 mol/mol.hr.

Example III

An experiment was carried out in the manner as outlined above, whereby as phosphine 4 mmol (1.42 g) of bis(3-chlorophenyl)(6-chloro-2-pyridyl)phosphine and as protonic acid 5 mmol (325 µl) of methanesulfonic acid were used. The feed was propyne, containing 3.6% of propadiene. The reaction temperature was 80° C.

The reaction time was 1 hour. Analysis showed that MMA had been formed with a selectivity of 99.6% at a propyne conversion of about 100%. The average reaction rate was calculated to be 12,000 mol/mol.hr.

Example IV

An experiment was carried out in the manner as outlined above, whereby as phosphine 2 mmol (0.71 g) of bis(3- chlorophenyl)(6-chloro-2-pyridyl)phosphine and as protonic acid 2 mmol (180 μl) of trifluoromethanesulfonic acid were used. The feed was propyne, containing 5.1% of propadiene. The reaction temperature was 85° C.

The reaction time was 5 hours. Analysis showed that MMA had been formed with a selectivity of 99.6% at a propyne conversion of about 86%. The average reaction rate was calculated to be 12,500 mol/mol.hr.

These examples demonstrate that the catalyst systems of the present invention (alike the comparative catalyst system based on a non-substituted phosphine) are sufficiently stable at elevated temperatures.

In comparative Examples I(a) and II(a), with a non-substituted phosphine as catalyst component, the reaction rates for convening feedstocks containing propadiene are low even at high temperatures due to the (inhibitive) presence of the propadiene. In Examples I(b), II(b), and II(c), however, the use of the halogenated phosphines of the present invention results in considerably higher reaction rates. Indeed, in Examples III and IV, a feedstock comprising 3.6%, respectively 5.1% of propadiene was convened at high yield and selectivity.

We claim:

1. A carbonylation catalyst comprising:

a) a source of cations of one or more metals of Group VIII of the Periodic Table;

b) a phosphine of the general formula selected from the group consisting of $R^1R^2M-R-PR^3R^3$, and $R^2R^3M-R-PR^1R^3$, wherein $R^1$ represents a substituted or non-substituted 6-membered heteroaryl group having at least one imino nitrogen atom next to the carbon atom that is attached to the phosphorus atom; $R^2$ represents a halogenated aryl group; $R^3$ or each of the $R^3$'s represents a substituted or non-substituted (hetero)hydrocarbyl group, M is an element of Group Va, R represents a bridging hydrocarbyl group having 1 to 4 carbon atoms in the bridge; and c) a source of protons.

2. The catalyst of claim 1, wherein the metal of component a) is selected from the group consisting of nickel, platinum and palladium.

3. The catalyst of claim 1, wherein the metal of component a) is palladium.

4. The catalyst of claim 1, wherein component b) comprises a phosphine wherein $R^1$ represents a 2-pyridyl group.

5. The catalyst of claim 1 wherein component b) comprises a phosphine wherein $R^2$ represents a phenyl group having one or more chlorine atoms substituted thereon.

6. A catalyst of claim 1 wherein component b) comprises a phosphine wherein $R^3$ or each of the $R^3$'s represents a substituted or non-substituted pyridyl, alkyl or aryl group.

7. A catalyst of claim 5 wherein component b) comprises a phosphine wherein both $R^2$ and $R^3$ represent a halogenated phenyl group.

8. A process for the carbonylation of acetylenically unsaturated compounds, the process comprising the steps of:

providing a feedstock, the feedstock comprising an acetylenically unsaturated compound and a relatively minor amount of an 1,2-alkadiene compound;

contacting the feedstock, under conditions effective to carbonylate the feedstock, with carbon monoxide and a hydroxylated co-reactant, in the presence of a catalyst system comprising a) a source of cations of one or more metals of Group VIII of the Periodic Table, b) a phosphine selected from the group consisting of $R^1R^2M-R-PR^3R^3$ and $R^2R^3M-R-PR^1R^3$, wherein $R^1$ represents a substituted or non-substituted 6-membered heteroaryl group having at least one imino nitrogen atom next to the carbon atom that is attached to the phosphorus atom; $R^2$ represents a halogenated aryl group; $R^3$ or each of the $R^3$'s represents a substituted or non-substituted (hetero)hydrocarbyl group, M is an element of Group Va, R represents a bridging hydrocarbyl group having 1 to 4 carbon atoms in the bridge, and c) a source of protons; and recovering the carbonylated feedstock.

9. The process of claim 8, wherein the amount of 1,2-alkadiene compound in the feedstock is less than 0.1 mole per mole of acetylenically unsaturated compound.

10. The process of claim 9, wherein the molar amount of 1,2-alkadiene compound in the feedstock per mole of acetylenically unsaturated compound is in the range of 0.002 to 0.05.

11. The process of claim 8 wherein the recovered carbonylated feedstock is methyl methacrylate and the feedstock comprises propyne and 1,2-propadiene.

* * * * *